United States Patent [19]

Zoche et al.

[11] 4,080,378

[45] Mar. 21, 1978

[54] PROCESS FOR THE PREPARATION OF CARBOXYLIC ACID CHLORIDES OF THE BENZENE SERIES

[75] Inventors: Günter Zoche, Bonn-Beuel; Hermann Richtzenhain, Much-Schwellenbach; Wilhelm Vogt, Cologne, all of Germany

[73] Assignee: Dynamit Nobel Aktiengesellschaft, Troisdorf, Germany

[21] Appl. No.: 737,368

[22] Filed: Nov. 1, 1976

[30] Foreign Application Priority Data

Nov. 4, 1975 Germany ............................. 2549242

[51] Int. Cl.² ............................................. C07C 51/58
[52] U.S. Cl. ........................... 260/544 D; 260/652 R; 260/664
[58] Field of Search ................... 260/544 D; 252/439, 252/441, 443, 467

[56] References Cited

U.S. PATENT DOCUMENTS

| 2,700,679 | 1/1955 | Carnahan et al. ................ 260/544 D |
| 3,835,187 | 9/1974 | Dyson .............................. 260/544 D |

FOREIGN PATENT DOCUMENTS

| 820,698 | 11/1937 | France ............................. 260/544 D |
| 1,954,793 | 5/1971 | Germany .......................... 260/544 X |
| 2,311,825 | 6/1973 | Germany .......................... 260/544 D |

*Primary Examiner*—Norman Morgenstern
*Attorney, Agent, or Firm*—Burgess, Dinklage & Sprung

[57] ABSTRACT

A process for preparing substituted or unsubstituted carboxylic acid chlorides of the benzene series which comprises contacting the corresponding carboxylic acid ester with an aromatic compound containing at least one nuclearly bound trichloromethyl group in the presence of a molybdenum catalyst.

16 Claims, No Drawings

PROCESS FOR THE PREPARATION OF CARBOXYLIC ACID CHLORIDES OF THE BENZENE SERIES

BACKGROUND OF THE INVENTION

1. Field of the Invention

The subject of the present invention is a process for the preparation of carboxylic acid chlorides of the benzene series by the reaction of the corresponding carboxylic acid esters with trichloromethylbenzenes in the presence of a catalyst.

2. Discussion of the Prior Art

It is known to prepare aromatic carboxylic acid chlorides from the corresponding carboxylic acid alkyl esters and trichloromethylbenzenes, using Lewis or Brönsted acids as catalysts, preferably the chlorides of zinc, aluminum, iron or sulfuric acid (cf. French Pat. No. 820,698 and German "Offenlegungsschrift" No. 1,954,793). Iron and aluminum are used as catalysts also in the preparation of aromatic carboxylic acid chlorides in which polyesters of aromatic carboxylic acids are reacted with trichloromethylbenzenes (German Offenlegungsschrift No. 2,311,825). It is important in all of the above-named processes that the competing Friedel-Crafts reaction be prevented insofar as possible.

The use of the above-named catalysts has several disadvantages: The reaction takes a very long time, and in some cases additional catalyst must be fed in constantly. The reaction times are long and the volume-time yields are, accordingly, low.

The problem has therefore existed of devising a process for the preparation of the above-named carboxylic acid chlorides which will result in higher yields of the desired carboxylic acid chloride with shorter reaction times and, insofar as possible, low temperatures.

SUMMARY OF THE INVENTION

Broadly this invention contemplates a process for preparation of substituted or unsubstituted carboxylic acid chlorides of the benzene series by a process comprising contacting a corresponding carboxylic acid ester, including a high molecular weight ester, with an aromatic compound containing at least one nuclearly bound trichloromethyl group in the presence of a molybdenum catalyst. At the heart of the present invention there is the use of a molybdenum catalyst. The molybdenum catalyst can be in the form of elemental molybdenum, e.g., metal powder, or can be in the form of a molybdenum compound such as molybdenum oxide. Other compounds of molybdenum are also contemplated as catalysts for the preparation of the carboxylic acid chlorides, the reaction of the corresponding carboxylic acid esters with an aromatic compound containing a nuclearly bound trichloromethyl group.

When these substances are used as catalysts, one can operate at temperatures between 140° and 190° centigrade and obtain within three to four hours yields of more than 90 percent in the preparation of terephthalic acid chlorides. The amount of catalyst used is considerably smaller than in the known methods. Amounts of 0.1 to 10 grams, and preferably 0.5 to 1.0 grams, per mole of the trichloromethyl group suffice.

In addition to metallic molybdenum, virtually all of the known molybdenum compounds can be used as catalyst, such as, for example, the chalcogenides, halides and hydroxyhalides, the carbonyl compounds, or the molybdates. Molybdenum trioxide ($MoO_3$) is used preferentially. Specific molybdenum compounds include:

$MoBr_3$, $MoCl_2$, $MoCl_5$, $MoO_2Cl_2$, $Mo(CO)_6$, $Na_2MoO_4(2H_2O)$, $(NH_4)_6Mo_7O_{24} \cdot 4H_2O$, dioxobis(2,4-pentanedionato-O,O')-molybdenum ($C_{10}H_{14}MoO_6$).

The aromatic carboxylic acid alkyl esters which can be used as starting compounds include esters of mono- and dicarboxylic acids as well as those of tricarboxylic acids, and when dicarboxylic and tricarboxylic acid esters are used the carboxylic acid ester groupings can be in either the ortho or in the meta or para position with respect to one another. The aromatic nucleus can also contain additional substituents, such as $C_{1-18}$ alkyl or alkoxy groups or halogens.

Examples of usable carboxylic acid esters are: toluylic acid methyl esters, toluylic acid ethyl esters, toluylic acid 2-methoxy-ethyl esters, ethylbenzoic acid alkyl esters, chlorobenzoic acid ethyl esters, trichlorobenzoic acid alkyl esters, the alkyl esters of benzoic acid with long alkyl or alkoxy radicals in the nucleus, such as those of dodecylbenzoic acid, dodecoxy benzoic acid or octadecylbenzoic acid. Of the dicarboxylic acid esters we shall mention especially phthalic acid dimethyl ester, isophthalic acid dimethyl ester and terephthalic acid dimethyl ester.

Where reference is made to an alkyl ester preferably the alkyl group has 1–8 carbon atoms, especially 1–4 carbon atoms. Where reference is made to an alkyl group on the nucleus, the alkyl group is 1–18 carbon atoms. The term "long alkyl" refers to $C_{10}$–$C_{18}$ alkyl groups. Where reference is made to "alkoxy" the alkyl group thereof is 1–8 carbon atoms preferably.

The ester grouping can accordingly be based on a monovalent alcohol of 1 to 8 carbon atoms containing, if desired, an oxygen or sulfur atom in the chain. In addition to the esters of mono-, di- and tricarboxylic acids with monovalent alcohols, esters of these carboxylic acids with polyvalent alcohols can also be used. Such esters are, for example, the esters of the aromatic dicarboxylic acids with bivalent alcohols, such as ethylene glycol, propylene glycol, tetramethylene glycol, and cyclohexanedimethanol. Preferred are the polyesters which can be prepared from the above dicarboxylic acids and diols, such as, for example, polypropylene terephthalate, polytetramethylene isophthalate, polypropylenediphenyldicarboxylate, and poly-1,4-cyclohexanedicarbinolterephthalate. Of special interest here is the recycling of any wastes containg the above mentioned polyesters.

The trichloromethylbenzenes which can be used as additional starting products include mono, bis and tris-(trichloromethyl) benzenes, which can also be substituted by chlorine. Examples are o-, m- and p-chlorobenzotrichlorides, m- and p-bis-(trichloromethyl) benzenes, 1,3-bis-(trichloromethyl)-5-chlorobenzene, the bis-(trichloromethyl) dichlorobenzenes, and o-dichloromethyltrichloromethylbenzene.

The reaction of the invention can be performed without the use of solvents, providing the compounds are fluid at the reaction temperature. It is also possible, however, to perform it in an inert organic solvent, such as for example the chlorobenzenes, toluene, xylene, or diphenyl.

The trichloromethyl component is preferably used in an equimolar ratio to the carboxylic acid ester. Fundamentally one can use a slight excess of up to 10 percent.

The alkyl chloride forming in the reaction is best removed from the reaction mixture by distillation during the reaction, and can then be used as-is, as an intermediate product.

Upon completion of the reaction, the carboxylic acid chloride is removed by distillation, preferably in vacuo.

EXAMPLES 2 to 7

The rest of the examples were performed similarly to Example 1 and are reviewed in the following table.

| Example No. | Starting Materials Ester | Trichloromethyl aromatic compound | Catalyst | Reaction temp. and time | Product (Yield) |
|---|---|---|---|---|---|
| 1 | Dimethylterephthalate 777 g (4 moles) | 1,4-bis-(trichloromethyl)-benzene 1252 g (4 moles) | $MoO_3$ 4 g | 170–175° C 3 h | Terephthalic acid dichloride 1559 g (95.8%) 398 g $CH_3Cl$ (98.5%) |
| 2 | Dimethylisophthalate 194 g (1 mole) | 1,3-bis-(trichloromethyl)-benzene 313 g (1 mole) | Mo (metal powder) 1 g | 155–165° C 4 h | Isophthalic acid dichloride 378 g (93.0%) 93 g $CH_3Cl$ (92.1%) |
| 3 | Polyethyleneterephthalate 192 g (1 mole-unit) | 1,4-bis-(trichloromethyl)-benzene 313 g (1 mole) | $MoCl_5$ 2 g | 170–180° C 2 h | Terephthalic acid dichloride 380 g (93.6%) 90 g ethylene chloride (91.0%) |
| 4 | Polyethyleneterephthalate (cellulose silk waste) 192 g (1 mole-unit) | 1,4-bis-(trichloromethyl)-benzene 313 g (1 mole) | $MoO_3$ 1 g | 170–175° C 2 h | Terephthalic acid dichloride 362 g (89.1%) 86 g ethylene chloride (86.9%) |
| 5 | p-Toluylic acid methyl ester 600 g (4 moles) | 1,4-bis-(trichloromethyl)-benzene 689 g (2.2 moles) | $MoO_3$ 2 g | 175–180° C 6 h | p-Toluylic acid chloride 495 g (80.0%) |
| 6 | p-Toluylic acid methyl ester 600 g (4 moles) | 1,4-bis-(trichloromethyl)-benzene 626 g (2 moles) | $MoO_3$ 2 g | 160–170° C 11 h | p-Toluylic acid chloride 562 g (90.9%) 183 g $CH_3Cl$ (90.6%) |
| 7 | p-Chlorobenzoic acid methyl ester 85 g (0.5 mole) | p-Chlorobenzotrichloride 115 g (0.5 mole) | $MoO_3$ 0.5 g | 160–170° C 3 h | p-Chlorobenzoyl chloride 167 g (95.4%) 22 g $CH_3Cl$ (87.1%) |

The monofunctional acid chlorides that can be prepared by the present process can easily be transformed to the corresponding peroxides, which are used as polymerization catalysts. These acid chlorides can easily be reduced by the Rosenmund reaction to the corresponding aldehydes which are used as intermediates in the preparation of pharmaceuticals (e.g., antibiotics, tranquilizers). Terephthalic acid dichloride and isophthalic acid dichloride are furthermore used for the preparation of polyamides and polyaryl esters of high molecular weight.

The reaction of the benzene carboxylic acid ester with the trichloromethyl containing aromatic compound can be conducted over a broad range of process parameters. Generally speaking the temperature is between 110 and 250° C, preferably between 140° and 190° C. In a preferred embodiment the reaction is conducted at atmospheric pressure at a temperature between 140° and 190° C for between three and four hours. In order to more fully illustrate the nature of the invention and the manner of practicing the same, the following examples are presented:

EXAMPLE 1

A two-liter round flask, equipped with thermometer, magnetic stirrer, Vigreux column (40 cm), fractionating column, air cooler and receiver, was filled with 777 g (4 moles) of dimethylterephthalate, 1252 g (4 moles) of 1,4-bis-(trichloromethyl)-benzene and 4 g of molybdenum trioxide. The flask contents were maintained for 3 hours at 170° to 175° C. The escaping methyl chloride was captured in a cooling trap following the receiver. In the vacuum distillation that followed, 1559 g of terephthalic acid was obtained in a purity of 99.8% (GC). This corresponds to a yield of 95.8%.

During the reaction, 398 g of methyl chloride was captured in the cooling trap, which corresponds to a yield of 98.5%.

What is claimed is:

1. In a process for the preparation of a substituted or unsubstituted carboxylic acid chloride of the benzene series by reaction of the corresponding carboxylic acid ester with an aromatic compound containing at least one nuclearly bound trichloromethyl group in the presence of a catalyst, the improvement wherein molybdenum or molybdenum compound is employed as the catalyst.

2. A process according to claim 1 wherein the molybdenum catalyst is a chalcogenide, halide or carbonyl of molybdenum.

3. A process according to claim 1 wherein a molybdate is employed as the molybdenum compound.

4. A process according to claim 1 wherein elemental molybdenum is employed as the catalyst.

5. A process according to claim 4 wherein elemental molybdenum is in the form of a powder.

6. A process according to claim 1 wherein $MoO_3$ is employed as the molybdenum catalyst.

7. A process according to claim 1 wherein the molybdenum catalyst is employed in an amount of 0.01 to 10 g per mole of trichloromethyl group charged.

8. A process according to claim 1 wherein the molybdenum catalyst is employed at an amount of 0.5 to 1.0 g per mole of trichloromethyl group charged.

9. A process according to claim 8 wherein the process is conducted at a temperature between 140° and 190° C.

10. A process according to claim 9 wherein the process is conducted in a period of time from 3 to 4 hours.

11. A process according to claim 1 wherein the carboxylic acid ester reactant is toluylic acid methylester, toluylic acid ethyl ester, toluylic acid 2-methoxy-ethyl ester, an ethylbenzoic acid alkyl ester, chlorobenzoic acid ethyl ester, a trichlorobenzoic acid alkyl ester, or an alkyl ester of benzoic acid having a long alkyl or alkoxy radical in the nucleus.

12. A process according to claim 1 wherein the carboxylic acid alkyl ester reactant contains a substituent on the aromatic nucleus which substituent is a $C_{1-18}$ alkyl or alkoxy group or a halogen.

13. A process according to claim 1 wherein the aromatic compound containing the trichloromethyl group is a trichloromethylbenzene.

14. A process according to claim 13 wherein the trichloromethylbenzene compound is a mono, bis, or tris (trichloromethyl) benzene which can be substituted nuclearly by chlorine.

15. A process according to claim 14 wherein the trichloromethylbenzene compound is o-, m- or p-chlorobenzotrichloride, m- or p-bis-(trichloromethyl) benzene, 1,3-bis-(trichloromethyl)-5-chlorobenzene, bis-(trichloromethyl) dichlorobenzene or o-dichloromethyltrichloromethylbenzene.

16. A process according to claim 1 wherein a molybdenum compound is employed said molybdenum compound being molybdenum pentachloride.